United States Patent
Chen et al.

(10) Patent No.: US 9,040,274 B2
(45) Date of Patent: May 26, 2015

(54) METHOD FOR INCREASING PROTEIN THERMAL STABILITY

(71) Applicants: Jian Chen, Wuxi (CN); Guocheng Du, Wuxi (CN); Xinyao Lu, Wuxi (CN); Song Liu, Wuxi (CN); Juan Zhang, Wuxi (CN)

(72) Inventors: Jian Chen, Wuxi (CN); Guocheng Du, Wuxi (CN); Xinyao Lu, Wuxi (CN); Song Liu, Wuxi (CN); Juan Zhang, Wuxi (CN)

(73) Assignee: Jiangnan University, Wuxi, JS (CN)

( * ) Notice: Subject to any disclaimer, the term of this patent is extended or adjusted under 35 U.S.C. 154(b) by 0 days.

(21) Appl. No.: 13/870,509

(22) Filed: Apr. 25, 2013

(65) Prior Publication Data

US 2014/0322788 A1    Oct. 30, 2014

(30) Foreign Application Priority Data

May 10, 2012    (CN) .............................. 201210145190

(51) Int. Cl.
*C12N 9/96* (2006.01)
*C12N 9/02* (2006.01)
*C12N 9/26* (2006.01)
*C12N 9/10* (2006.01)

(52) U.S. Cl.
CPC ................ *C12N 9/96* (2013.01); *C12N 9/0069* (2013.01); *C12N 9/1044* (2013.01); *C12N 9/2411* (2013.01)

(58) Field of Classification Search
None
See application file for complete search history.

(56) References Cited

U.S. PATENT DOCUMENTS

| | | | |
|---|---|---|---|
| 2006/0263855 A1* | 11/2006 | Wood et al. | 435/69.7 |
| 2008/0095758 A1* | 4/2008 | Lee et al. | 424/94.63 |
| 2011/0224139 A1* | 9/2011 | Segers et al. | 514/9.4 |
| 2011/0237435 A1* | 9/2011 | Ryan | 504/196 |
| 2014/0255712 A1* | 9/2014 | Ostermann et al. | 428/474.4 |

OTHER PUBLICATIONS

Lin et al., "Self-assembling amphipathic alpha-helical peptides induce the formation of active protein aggregates in vivo", Faraday Discussions, vol. 166, pp. 243-256, 2013.*
Wu et al., "Active protein aggregates induced by terminally attached self-assembling peptide ELK16 in *Escherichia coli*", Microbial Cell Factories, vol. 10, No. 9, pp. 1-8, 2011.*
Satakarni et al., "Enrichment of fermentation media and optimization of expression conditions for the production of EAK16 peptide as fusions with SUMO", Biotechnology and Bioengineering, vol. 102, No. 3, pp. 725-735, 2009.*
Riley et al., "Bioproduction and characterization of a pH responsive self-assembling peptide", Biotechnology and Bioengineering, vol. 103, No. 2, pp. 241-251, 2009.*
Chinese Application No. 201210145190.7, filed May 10, 2012.*
Zhang S, Lockshin C, Cook R, and Rich A. Unusually stable beta-sheet formation in an ionic self-complementary oligopeptide. Biopolymers, 1994, 34:663-672.
Tian J, Wang P, Wu NF, and Fan YL Recent advances in the rational design to improve the protein thermostability. Current Biotechnology. 2012, 2(4): 233-239.

* cited by examiner

*Primary Examiner* — Rebecca Prouty
*Assistant Examiner* — Richard Ekstrom
(74) *Attorney, Agent, or Firm* — Lili Chen

(57) ABSTRACT

The invention provides a simple and effective method for increasing thermal stability of a wide range of proteins, comprising fusing a self-assembling amphipathic peptide to the C- or N-terminal of target proteins. The fusion protein can have a half life up to 26 times longer than that of the wild type protein.

2 Claims, No Drawings

METHOD FOR INCREASING PROTEIN THERMAL STABILITY

CROSS-REFERENCES AND RELATED APPLICATIONS

This application claims priority of Chinese Application No. 201210145190.7, entitled "A method for increasing protein thermal stability", filed May 12, 2012, which is herein incorporated by reference in its entirety.

BACKGROUND OF THE INVENTION

1. Field of the Invention

The present invention relates to a method for increasing thermal stability of recombinant proteins, and more particularly relates to a method of increasing thermal stability of target proteins by fusing self-assembling amphipathic peptides (SAPs) to their N- or C-terminal.

2. Description of the Related Art

Self-assembling amphipathic peptides are a category of peptides that have unique sequences with alternating hydrophobic and hydrophilic residues and can spontaneously assemble into ordered nanostructures. These peptides can increase activity and stability of enzymes through hydrogenation.

To date, a vast number of enzymes isolated from different organisms are widely used in industrial productions. In order to achieve a wider range of applications of industrial enzymes, improving thermal stability of these enzymes is imperative. There were several methods used for improving thermal stability of enzymes, such as: 1) directed molecular evolution, which uses site-directed, random or saturated mutagenesis to look for enzymes with increased thermal stability. This method is depends on the analysis of crystal structure or establishment of a high throughput screening assay. 2) identification and isolation of thermal stability of enzymes from thermophilic microorganisms. However, these methods have limitations and can not be suitable for improving of thermal stability of all the enzymes. There is a need to develop simple and effective methods suitable for increasing thermal stability of a wide spectrum of proteins. The present invention satisfies this need and provides other benefits as well.

DETAILED DESCRIPTION

The present invention provides a method for increasing thermal stability of a recombinant protein, comprising fusing a self-assembling amphipathic peptide (SAP) to N- or C-terminal of the recombinant protein.

The method comprises the following steps:

1. Construction of Plasmids with SAPs Genes

The DNAs encoding SAPs were chemically synthesized. Each SAP gene was cloned into the Nde I-NcoI site of the pET-22b(+) plasmid, yielding the pET-22b(+)/AP plasmid containing a SAP gene.

2. Construction of Expression Plasmids of Recombinant Proteins Fused with SAPs

The gene encoding a recombinant protein was cloned into NdeI-Hind III site of a pET-22b(+)/AP plasmid in frame with the SAP, and the pET-22b(+)/AP-enzyme plasmid that expresses the protein-SAP fusion protein was constructed.

3. Construction of Genetic Modified Bacteria Strain for Expressing SAP Fusion Protein The pET-22b(+)/AP-enzyme plasmids with SAP fusion proteins were individually transformed into E. coli Rosetta (DE3), and transgenic E. coli with inducible and high levels of expression of SAP fusion proteins were constructed.

The method for culturing the E. coli strain expressing SAP fusion protein is as follows:

Medium Composition:

Seed culture medium: peptone 10 g/L; yeast extract 5 g/L; NaCl 5 g/L;

Fermentation medium: peptone 12 g, yeast extract 24 g, and glycerin 4 ml are dissolved in 900 ml water and sterilized at high pressure. When the medium is cooled to 60° C., a sterilized solution (100 mL) containing 0.17 mol/L $KH_2PO_4$ and 0.72 mol/L $K_2HPO_4$ is added to it. The sterilized solution is prepared as follows: $KH_2PO_4$ 2.31 g and $K_2HPO_4$ 12.54 g are dissolved in 100 mL water, and the solution is sterilized by high pressure or by filtration through 0.22 μm filter membrane.

Culture Method:

Seed culture: a single clone of an E. coli strain expressing a SAP fusion protein was inoculated into 25 mL of seed culture medium in a 250 mL flask, and grew at 37° C., 200 rpm for 12 hours.

Fermentation culture: 2.5 ml of the above E. coli seed culture was inoculated to 25 mL fermentation solution (10% inoculum rate) in a 250 mL flask, and grew at 37° C. until the optical density at 600 nm ($OD_{600}$) achieved 0.6. The culture temperature was then changed to 16° C., and IPTG was added to a final concentration of 1 mM to induce the expression of the SAP fusion protein.

The method for accessing thermal stability of recombinant protein

The thermal stability of a recombinant enzyme was determined by measuring the remaining activity after incubating the enzyme solution at a selected temperature. The thermal stability of the enzymes was represented by the half-life of the enzymes at the selected temperature. A half-life of an enzyme is the time required for the enzymatic activity to fall to half of its initial value at certain temperatures. The half life of a enzyme-SAP fusion protein is compared with that of the wild type enzyme without fusion to any SAP.

The present invention provides a method for increasing thermal stability of recombinant proteins. The method comprises fusing a self-assembling amphipathic peptide to C- or N-terminal of a recombinant protein, and generating a SAP fusion protein with increased thermal stability. This method can significantly increase the thermal stability of a wide range of proteins, is simple to operate, and can easily scale up to industrial scale production of enzymes. The invention provides a simple and effective method for increasing the thermal stability of proteins thus facilitating their usage in industrial applications.

EXAMPLES

The following examples were provided by way of illustration only, and not by way of limitation. Standard experimental operations not specifically described in the specification were preformed according to standard molecular cloning protocols described in "Molecular Cloning: A Laboratory Manual" (by Sambrook J and Russell D, Cold Spring Harbor Laboratory Press, 3rd Edition, 2001).

Material and method: All the restriction endonucleases, T4 DNA ligation enzyme, PCR reagents, and DNA markers etc., were purchased from Takara (Dalian, China). Competent cells of E. coli JM109, primers, plasmid extraction kit, and gel DNA purification kit were purchased from Sangon (Shanghai, China).

Example 1

Construction of pET-22b(+)/AP Plasmids Having SAP Genes

Examples of the self-assembling amphipathic peptide sequences used for fusing with target proteins to increase their thermal stability are provided below as SEQ ID Nos: 1 to 6.

```
SEQ ID No: 1:
AEAEAKAKAEAEAKAK

SEQ ID No: 2:
VNYGNGVSCSKTKCSVNWGQAFQERYTAGTNSFVSGVSGVASGA

GSIGRR

SEQ ID No: 3:
DWLKAFYDKVAEKLKEAFKVEPLRADWLKAFYDKVAEKLKEAF

SEQ ID No: 4:
DWLKAFYDKVAEKLKEAFGLLPVLEDWLKAFYDKVAEKLKEAF

SEQ ID No: 5:
DWLKAFYDKVAEKLKEAFKVQPYLDDWLKAFYDKVAEKLKEAF

SEQ ID No: 6:
DWLKAFYDKVAEKLKEAFNGGARLADWLKAFYDKVAEKLKEAF
```

The DNA encoding each SAP sequence, as shown above, was chemically synthesized, and cloned into the NdeI-NcoI site of the pET-22b(+) plasmid according to standard molecular cloning protocols as described in "Molecular Cloning: A Laboratory Manual". The pET-22b(+) plasmids containing SAP genes were named as pET-22b(+)/AP plasmids.

Example 2

Construction of pET-22b(+)/AP-Enzyme Plasmid Containing SAP Fusion Protein/Enzyme Target proteins/enzymes in frame with SAP genes were cloned into Nco I-Hind III site of pET-22b(+)/AP plasmids, and the pET-22b(+)/AP-enzyme plasmids that can express the SAP fusion proteins were constructed. These pET-22b(+)/AP-enzyme plasmids were individually transformed into *E. coli* JM109. The transformation protocol is as follows:

(1) Take 200 µL competent cells of *E. coli* JM109 under sterile condition, and add the cells to a sterile microcentrifuge tube.

(2) Add the pET-22b(+)/AP-enzyme plasmid (1-2 µL) to the tube with *E. coli* JM109 cells, mix gently, and incubate on ice for at least 30 minutes.

(3) Remove the tube from the ice and immediately put them in the 42° C. hot block for exactly 90 seconds.

(4) Quickly return the tubes to ice and incubate for 1-2 minutes.

(5) Add 0.8 ml of LB medium without antibiotic to the tube.

(6) Plate 200 µL of the above LB medium on a LB plate with Ampicillin. The plate is incubated upside up at 37° C. for 20 minutes until extra liquid is absorbed by the plate. It is then incubated upside down overnight at 37° C.

In the next morning, pick single colonies formed on the LB plate and confirm by PCR and DNA sequencing that the colonies contain the correct target sequence.

Example 3

Construction of *E. coli* Strains for Expressing SAP Fusion Proteins

Each pET-22b(+)/AP-Enzyme plasmid was transformed into *E. coli* BL21(DE3) cells to make *E. coli*. strains expressing SAP fusion proteins. The transformation protocol is as follows:

(1) Take 200 µL competent cells of *E. coli* BL21 (DE3) under sterile condition, and add the cells to a sterile microcentrifuge tube.

(2) Add the pET-22b(+)/AP-enzyme plasmid (1-2 µL) to the tube with *E. coli* BL21 (DE3) cells, mix gently, and incubate on ice for at least 30 minutes.

(3) Remove the tube from the ice and immediately put them in the 42° C. hot block for exactly 90 seconds.

(4) Quickly return the tubes to ice and incubate for 1-2 minutes.

(5) Add 0.8 ml of LB medium without antibiotic to the tube.

(6) Plate 200 µL of the above LB medium on a LB plate with Ampicillin. The plate is incubated upside up at 37° C. for 20 minutes until extra liquid is absorbed by the plate. It is then incubated upside down overnight at 37° C.

In the next morning, pick single colonies formed on the LB plate and confirm by PCR and DNA sequencing that the colonies contain the correct target sequence.

Example 4

Production of lipoxygenase-SAP Fusion Protein

Lipoxygenase gene (Genebank ID NO:PA119) was fused to each of six SAP genes (in Example 1) to make the pET-22b(+)/AP-Lipoxygenase plasmid by methods described in Example 2 and 3. The *E. coli* BL21 (DE3) transformed by the pET-22b(+)/AP-Lipoxygenase plasmid was used for producing lipoxygenase-SAP fusion protein.

The procedure for culturing the *E. coli* cells is as follows:

Medium Composition:

Seed culture medium: peptone 10 g/L, yeast extract 5 g/L, and NaCl 5 g/L.

Fermentation medium: peptone 12 g, yeast extract 24 g, and glycerin 4 ml are dissolved in 900 ml water and sterilized at high pressure. When the medium is cooled to 60° C., a sterilized solution (100 mL) containing 0.17 mol/L $KH_2PO_4$ and 0.72 mol/L $K_2HPO_4$ is added into it. The sterilized solution is prepared as follows: $KH_2PO_4$ 2.31 g and $K_2HPO_4$ 12.54 g are dissolved in 100 mL water, and the solution is sterilized by high pressure or by filtration through 0.22 µm filter membrane.

Culture Method:

Seed culture: a single clone of an *E. coli* BL21(DE3) strain expressing a SAP fusion protein was inoculated to 25 mL seed culture medium in a 250 mL flask, and incubated at 37° C., 200 rpm for 12 hours.

Fermentation culture: 2.5 ml of the above *E. coli* BL21 (DE3) was inoculated to 25 mL fermentation medium in a 250 mL flask. The culture was incubated at 37° C. until the optical density at 600 nm ($OD_{600}$) achieved 0.6. The culture temperature was then changed to 16° C., and IPTG was added to a final concentration of 1 mM to induce the expression of the SAP fusion protein. The culture was incubated at 16° C. for additional 24 hours.

*E. coli* BL21(DE3) cells with the pET-22b(+)/AP-Lipoxygenase plasmid were harvested from the fermentation broth by centrifugation (15000 rpm, 10 min), and lysed in a Tris buffer solution (150 mM Tris-Hcl, pH 7.5). The lipoxygenase-SAP fusion protein were purified sequentially by hydrophobic chromatography, ion exchange chromatography, and gel electrophoresis. The thermal stability of the fusion protein or the control protein without a SAP fusion was represented by its half-life at 50° C. The results are shown in Table 1. The numbers in the table correspond to the SEQ ID NOs in Example 1.

TABLE 1

Thermal stability of the wild-type lipoxygenases (control)
and SAP-lipoxygenase fusion proteins at 50° C.

| | Control | 1 | 2 | 3 | 4 | 5 | 6 |
|---|---|---|---|---|---|---|---|
| T½ (min) | 10 | 18 | 39 | 38 | 22 | 252 | 187 |

Example 5

Production of Alkaline Amylase-SAP Fusion Protein

Alkaline amylase (Genebank ID NO: HV220894.1) was fused to each of six SAP genes as listed in Example 1 to make the pET-22b(+)/AP-Alkaline amylase plasmid by methods described in Examples 2 and 3. The E. coli BL21 (DE3) transformed by the pET-22b(+)/AP-Alkaline amylase plasmid was used for producing Alkaline amylase-SAP fusion protein.

The procedure for culturing the E. coli cells is as follows:
Medium Composition:
Seed culture medium: peptone 10 g/L, yeast extract 5 g/L, and NaCl 5 g/L.
Fermentation medium: peptone 12 g, yeast extract 24 g, and glycerin 4 ml are dissolved in 900 ml water and sterilized at high pressure. When the medium is cooled to 60° C., a sterilized solution (100 mL) containing 0.17 mol/L $KH_2PO_4$ and 0.72 mol/L $K_2HPO_4$ is added into it. The sterilized solution is prepared as follows: $KH_2PO_4$ 2.31 g and $K_2HPO_4$ 12.54 g are dissolved in 100 mL water, and the solution is sterilized by high pressure or filtration through 0.22 μm filter membrane.
Culture Method:
Seed culture: a single clone of an E. coli BL21(DE3) strain expressing a SAP fusion protein was inoculated to 25 mL seed culture medium in a 250 mL flask, and grew at 37° C., 200 rpm for 12 hours.
Fermentation culture: 2.5 ml of the above E. coli BL21 (DE3) was inoculated to 25 mL fermentation medium in a 250 mL flask, and incubated at 37° C. until the optical density at 600 nm ($OD_{600}$) achieved 0.6. The culture temperature was then changed to 16° C., IPTG was added to a final concentration of 1 mM to induce the expression of the SAP fusion protein, and the culture was incubated for 24 hours.

E. coli BL21(DE3) cells with the pET-22b(+)/AP-Alkaline amylase plasmid were harvested from the fermentation broth by centrifugation (15000 rpm, 10 min), and lysed in a Tris buffer solution (150 mM Tris-HCl, pH 7.5). The Alkaline amylase-SAP fusion protein were purified sequentially by hydrophobic chromatography, ion exchange chromatography, and gel electrophoresis. The thermal stability of the fusion protein or the control protein without a SAP fusion was represented by its half-life at 60° C. The results are shown in Table 2. The numbers (1-6) in the table correspond to the SEQ ID NOs 1 to 6 in Example 1.

TABLE 2

Thermal stability of the wild-type Alkaline amylase (control)
and Alkaline amylase-SAP fusion protein at 60° C.

| | Control | 1 | 2 | 3 | 4 | 5 | 6 |
|---|---|---|---|---|---|---|---|
| T½ (min) | 25 | 40 | 60 | 57 | 80 | 350 | 300 |

Example 6

Production of Transglutaminase-SAP Fusion Protein

Transglutaminase (Genebank ID NO: AF531437) was fused to each of six SAP genes as listed in Example 1 to make the pET-22b(+)/AP-Transglutaminase plasmid by methods described in Examples 2 and 3. The E. coli BL21 (DE3) transformed by the pET-22b(+)/AP-Transglutaminase plasmid was used for producing Transglutaminase-SAP fusion protein.

The procedure for culturing the E. coli cells is as follows:
Medium Composition:
Seed culture medium: peptone 10 g/L; yeast extract 5 g/L; NaCl 5 g/L;
Fermentation medium: peptone 12 g, yeast extract 24 g, and glycerin 4 ml are dissolved in 900 ml water and sterilized at high pressure. When the medium is cooled to 60° C., a sterilized solution (100 mL) containing 0.17 mol/L $KH_2PO_4$ and 0.72 mol/L $K_2HPO_4$ is added into it. The sterilized solution is prepared as follows: $KH_2PO_4$ 2.31 g and $K_2HPO_4$ 12.54 g are dissolved in 100 mL water, and the solution is sterilized by high pressure or filter-sterilized by 0.22 μm filter membrane.
Culture Method:
Seed culture: a single clone of an E. coli BL21(DE3) strain expressing a SAP fusion protein was inoculated to 25 mL seed culture medium in a 250 mL flask, and the culture was incubated at 37° C., 200 rpm for 12 hours.
Fermentation culture: 2.5 ml of the above E. coli BL21 (DE3) was inoculated to 25 mL fermentation medium in a 250 mL flask, and grew at 37° C. until the optical density at 600 nm ($OD_{600}$) achieved 0.6. The culture temperature was then changed to 16° C., IPTG was added to a final concentration of 1 mM to induce the expression of the SAP fusion protein, and the culture was incubated for 24 hours.

E. coli BL21(DE3) cells with the pET-22b(+)/AP-Transglutaminase plasmid were harvested from the fermentation broth by centrifugation (15000 rpm, 10 min), and lysed in a Tris buffer solution (150 mM Tris-Hcl, pH 7.5). The Transglutaminase-SAP fusion protein were purified sequentially by hydrophobic chromatography, ion exchange chromatography, and gel electrophoresis. The thermal stability of the fusion protein or the control protein without a SAP fusion was represented by its half-life at 50° C. The results are shown in Table 3. The numbers (1-6) in the table correspond to the SEQ ID NOs 1 to 6 in Example 1.

TABLE 3

Thermal stability of the wild-type transglutaminase (control)
and Transglutaminase-SAP fusion protein at 50° C.

| | Control | 1 | 2 | 3 | 4 | 5 | 6 |
|---|---|---|---|---|---|---|---|
| T½ (min) | 12 | 21 | 40 | 45 | 100 | 328 | 298 |

While the present invention has been described in some detail for purposes of clarity and understanding, one skilled in the art will appreciate that various changes in form and detail can be made without departing from the true scope of the invention. All figures, tables, appendices, patents, patent applications and publications, referred to above, are hereby incorporated by reference.

What is claimed is:

1. A method for increasing thermal stability of a target protein, comprising fusing a self-assembling amphipathic peptide (SAP) having an amino acid sequence set forth in SEQ ID NO:5 to said target protein by recombinant techniques to make a Target Protein-SAP fusion protein, wherein said Target protein-SAP fusion protein has increased thermal stability.

2. The method of claim 1, wherein said SAP is fused to N-terminal or C-terminal of said target protein.

* * * * *

```
                             SEQUENCE LISTING

<160> NUMBER OF SEQ ID NOS: 6

<210> SEQ ID NO 1
<211> LENGTH: 16
<212> TYPE: PRT
<213> ORGANISM: Unknown
<220> FEATURE:
<223> OTHER INFORMATION: Synthesized sequence

<400> SEQUENCE: 1

Ala Glu Ala Glu Ala Lys Ala Lys Ala Glu Ala Glu Ala Lys Ala Lys
1               5                   10                  15

<210> SEQ ID NO 2
<211> LENGTH: 50
<212> TYPE: PRT
<213> ORGANISM: Unknown
<220> FEATURE:
<223> OTHER INFORMATION: Synthesized Sequence

<400> SEQUENCE: 2

Val Asn Tyr Gly Asn Gly Val Ser Cys Ser Lys Thr Lys Cys Ser Val
1               5                   10                  15

Asn Trp Gly Gln Ala Phe Gln Glu Arg Tyr Thr Ala Gly Thr Asn Ser
            20                  25                  30

Phe Val Ser Gly Val Ser Gly Val Ala Ser Gly Ala Gly Ser Ile Gly
        35                  40                  45

Arg Arg
    50

<210> SEQ ID NO 3
<211> LENGTH: 43
<212> TYPE: PRT
<213> ORGANISM: Unknown
<220> FEATURE:
<223> OTHER INFORMATION: Synthesized sequence

<400> SEQUENCE: 3

Asp Trp Leu Lys Ala Phe Tyr Asp Lys Val Ala Glu Lys Leu Lys Glu
1               5                   10                  15

Ala Phe Lys Val Glu Pro Leu Arg Ala Asp Trp Leu Lys Ala Phe Tyr
            20                  25                  30

Asp Lys Val Ala Glu Lys Leu Lys Glu Ala Phe
        35                  40

<210> SEQ ID NO 4
<211> LENGTH: 43
<212> TYPE: PRT
<213> ORGANISM: Unknown
<220> FEATURE:
<223> OTHER INFORMATION: Synthesized sequence

<400> SEQUENCE: 4

Asp Trp Leu Lys Ala Phe Tyr Asp Lys Val Ala Glu Lys Leu Lys Glu
1               5                   10                  15

Ala Phe Gly Leu Leu Pro Val Leu Glu Asp Trp Leu Lys Ala Phe Tyr
            20                  25                  30

Asp Lys Val Ala Glu Lys Leu Lys Glu Ala Phe
        35                  40
```

```
<210> SEQ ID NO 5
<211> LENGTH: 43
<212> TYPE: PRT
<213> ORGANISM: unknown
<220> FEATURE:
<223> OTHER INFORMATION: Synthesized sequence

<400> SEQUENCE: 5

Asp Trp Leu Lys Ala Phe Tyr Asp Lys Val Ala Glu Lys Leu Lys Glu
1               5                   10                  15

Ala Phe Lys Val Gln Pro Tyr Leu Asp Asp Trp Leu Lys Ala Phe Tyr
            20                  25                  30

Asp Lys Val Ala Glu Lys Leu Lys Glu Ala Phe
        35                  40

<210> SEQ ID NO 6
<211> LENGTH: 43
<212> TYPE: PRT
<213> ORGANISM: unknown
<220> FEATURE:
<223> OTHER INFORMATION: Synthesized sequence

<400> SEQUENCE: 6

Asp Trp Leu Lys Ala Phe Tyr Asp Lys Val Ala Glu Lys Leu Lys Glu
1               5                   10                  15

Ala Phe Asn Gly Gly Ala Arg Leu Ala Asp Trp Leu Lys Ala Phe Tyr
            20                  25                  30

Asp Lys Val Ala Glu Lys Leu Lys Glu Ala Phe
        35                  40
```